United States Patent [19]

Brown et al.

[11] Patent Number: 4,590,799

[45] Date of Patent: May 27, 1986

[54] PIPELINE PIG TRACKING

[75] Inventors: Robert C. Brown, Ratho; John D. McIntyre, Musselburgh, both of Scotland

[73] Assignee: British Gas Corporation, London, England

[21] Appl. No.: 590,764

[22] Filed: Mar. 19, 1984

[30] Foreign Application Priority Data

Mar. 23, 1983 [GB] United Kingdom ............... 8307985

[51] Int. Cl.⁴ ............................................. G01M 7/00
[52] U.S. Cl. ......................... 73/432 R; 15/104.06 B; 200/61.41; 324/67
[58] Field of Search ............... 73/432 R, 432 V, 3, 73/623; 15/104.06 B; 324/67; 200/61.41

[56] References Cited

U.S. PATENT DOCUMENTS

| 2,601,249 | 6/1952 | Brenholdt | 15/104.06 B |
| 2,698,363 | 12/1954 | Rush | 15/104.06 B |
| 2,820,959 | 1/1958 | Bell | 15/104.06 B |
| 2,856,884 | 10/1958 | Savage | 15/104.06 B |

FOREIGN PATENT DOCUMENTS

0956075  9/1982  U.S.S.R. ................. 15/104.06 B

*Primary Examiner*—S. Leon Bashore
*Assistant Examiner*—K. M. Hastings
*Attorney, Agent, or Firm*—Larson and Taylor

[57] ABSTRACT

This invention relates to the tracking of a pipeline pig during its movement through a pipeline carrying gas, for instance.

The pig is tracked by detecting energy emission resulting from impact of the moving pig with at least two previously identified features which are located within the pipeline at known spaced intervals.

The energy emission takes the form of vibrational signals which are sensed by a geophone 1 which is coupled externally to the wall or associated equipment of a gas pipeline 2. An electrical output proportional to the vibration is amplified by a preamplifier 5 and is then filtered by a unit 6 to remove unwanted frequency components of the signal. The filtered signal is fed to a chart recorder 7. The unfiltered preamplified signal is fed to an audioamplifier 9 where the signal is amplified to audible levels.

8 Claims, 1 Drawing Figure

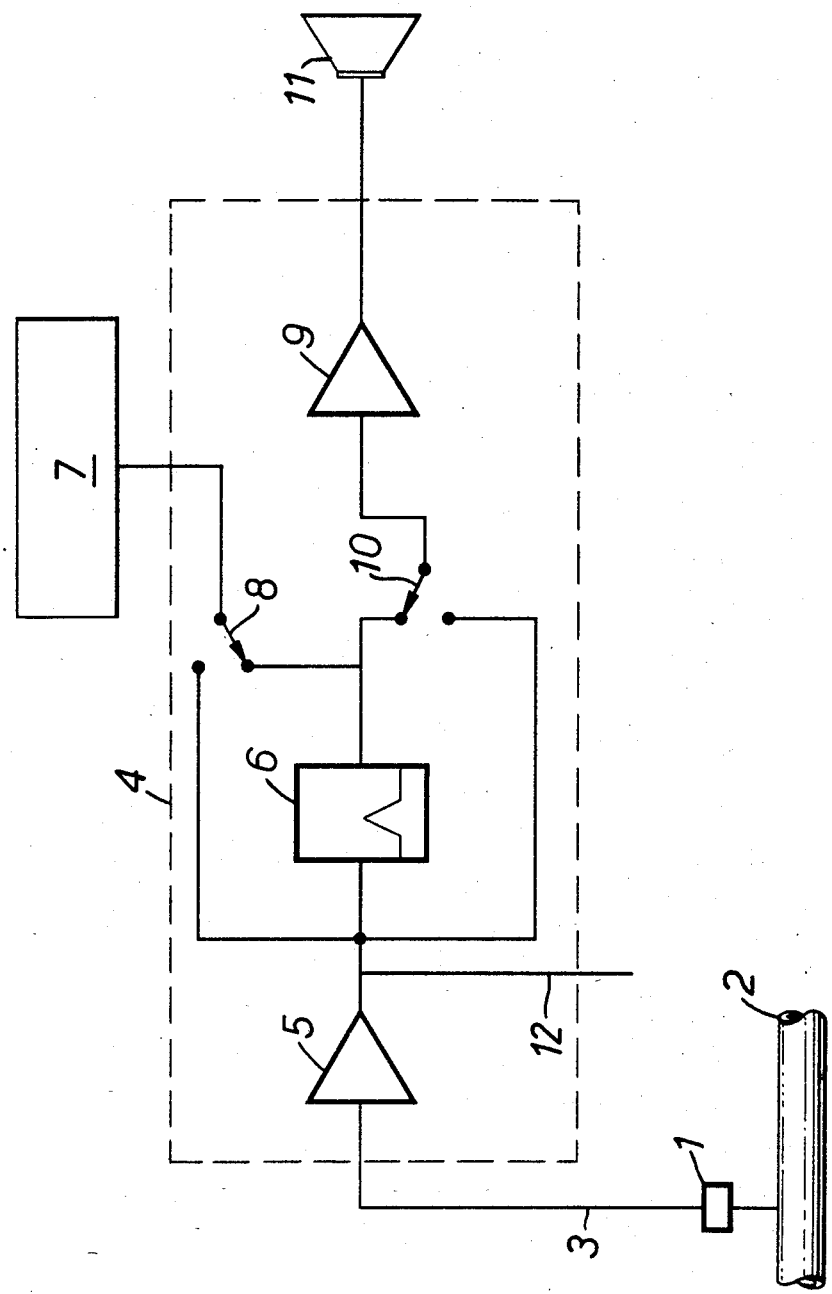

PIPELINE PIG TRACKING

The present invention relates to the tracking of a pipeline pig during its movement through a pipeline.

According to one aspect of the present invention there is provided a method for tracking a pipeline pig during its movement through a pipeline, the method comprising detecting energy emission resulting from impact of the moving pig with at least two previously identified features which are located within the pipeline at known spaced intervals.

According to another aspect of the present invention there is provided apparatus for tracking a pipeline pig during its movement through a pipeline, the apparatus comprising means for detecting energy emission resulting from impact of the moving pig with at least two previously identified features which are located within the pipeline at known spaced intervals.

The invention is directed to the tracking of multi-cupped pipeline pigs of the type which are propelled along the pipeline by the fluid flowing through the pipeline. These types of pigs are used extensively in the gas industry following pipeline construction and during on line pigging operations. The cups fitted to these pigs make contact with the internal surface of the pipeline and as the pig is propelled along the pipeline they impact with existing internal pipeline features such as weld beads, valves, bends etc. These impacts generate vibrational impulses which travel along the gas stream and the wall of the pipeline for detection at a tracking post. Providing that the location of such features is accurately known, it is possible to monitor the movement of the pig and track its passage along the pipeline by detecting and recording the time of occurrence of the impacts sequentially as energy impulses.

BRIEF DESCRIPTION OF THE DRAWING

An embodiment of the invention will now be particularly described with reference to the drawing which illustrates schematically suitable equipment for tracking a pipeline pig during movement through a pipeline.

The equipment comprises a sensor in the form of a geophone 1 which in use is magnetically or otherwise suitably coupled externally to the wall or associated equipment of a steel, gas or oil pipeline 2 in which the pig (not shown) is moving. The geophone 1 is electrically connected by means of an extension cable 3 to an amplifier/filter unit 4 (shown enclosed in dotted line).

The geophone 1 produces an electrical output proportional to the vibration produced by impact(s) of the moving pig with internal pipeline features. This signal is amplified by a pre-amplifier 5 forming part of the unit 4. The amplifier gain can be selected within a range. The amplified signal can be fed directly to a frequency filter unit 6 where unwanted frequency components in the signal are attenuated to enhance the peak value of the impact signal.

The filtered signal can then be fed to a visual display device such as a chart recorder 7.

Alternatively, instead of being filtered, the preamplified signal can be fed directly to the chart recorder 7. A switch 8 enables the appropriate mode to be selected.

The unfiltered pre-amplified signal can also be fed to an audio-amplifier 9 also forming part of the unit 4 where the signal is amplified to an adjustable power level which is readily audible depending on frequency.

Alternatively the filtered preamplified signal can be fed directly to the audio-amplifier 9. A switch 10 enables the appropriate mode to be selected.

On leaving the audio-amplifier 9 the amplified signal is fed to an audio-output device 11 in the form of a loudspeaker or headphones. The signal can also be directly tape-recorded.

Various preset centre frequencies can be selected on the filter unit 6 and this facility allows the system to be tuned to the various differing peak frequencies which vary with pipe diameter, wall thickness, fluid properties and other factors.

The filter unit 6 allows one of 24 preset centre frequencies (constant percentage band width) to be selected between 8 Hz and 1560 Hz allowing selection of a centre frequency which will optimise the pig signal to unwanted noise ratio.

The applicants have found that the peak signal received by the geophone is mainly dependent upon the natural frequency of oscillation of the pipeline structure to which the geophone is connected. The pipeline structure and the geophone are excited by broad-band background noise, ground-borne and air-borne, as well as by the pig-impact generated signal. Since the basic signal from the geophone is amplified, the filter unit provides a means for minimising the intrusion of unwanted background signals. The applicants have been able to formulate guidelines for frequency ranges of detection for some internal diameters of steel gas-conveying pipelines, namely 36" diameter pipeline—10 to 150 Hz, 24"—10 to 200 Hz and 12"—50 to 850 Hz. It must, however, be emphasised that these ranges are merely provided as a rough and ready guide and are by no means definitive.

The chart recorder 7 is a commercially available device compatible with the amplifier/filter unit 4 and having suitable writing and chart paper speeds for tracking. The recorder 7 inter alia indicates visually the time of occurrence of the impacts after allowing for any delay between the actual time of the impact and its reception. The delay time is determined by two factors, namely, the speed of sound in the fluid in the pipeline and the range of detection. For example, if the speed of sound in the fluid is 440 m/sec then the travel (delay) time for the signal per kilometer range is 1000 seconds = 2.272 seconds. Allowance for this effect can be built into the calculation for the estimate of position.

The signal, filtered or unfiltered, can be further analysed and processed by additional electronic circuit devices (not shown) to produce direct readout of variables eg. signal count, pig velocity etc. The signal from an output line 12 can also be digitised and conditioned for interfacing with computer devices.

If the arrival time at existing pipeline features is recorded and the distance between such features is known the pig average velocity and/or average acceleration can be computed between any selected sequential features as well as the location of the pig during its motion. Estimated times of arrival to downstream features can be predicted from these velocities.

The combination of an audible output and visual output enables the pipeline features with which the pig makes impact to be accurately identified. For example, we have found that where a bend, of say 22° or 45°, is negotiated by the pig, the signal in both the audio and visual outputs is substantially different to that received from single girth welds between pipe lengths. This means that known pipework configurations at special features like road and river crossings, block valves etc. are readily recognizable both audibly and visually from the outputs. The equipment therefore is deliberately designed to provide both an audible output to yield suitable pig movement information for tracking purposes.

We claim:

1. A method for tracking the movement of a pig along a length of pipeline from a first point to a second point spaced a substantial distance from the first point, the length of pipeline containing a number of internal features which are spaced along the length of pipeline at known locations between the first and second points and with which the pig sequentially makes an impact during the movement of the pig along the pipeline so as to generate a series of vibrational signals which correspond to the individual impacts and which are transmitted along the length of pipeline to the second point, the method comprising coupling to the wall of the pipeline at the second point a sensor for sensing the presence of any vibrational signal transmitted along the pipeline to the second point and producing an electrical output proportional to the respective vibrational signal, sensing a said vibrational signal and producing a corresponding said electrical output, and correlating the output produced with the respective internal feature with which the pig has made impact so as to estimate the position of the pig within the length of pipeline at any time.

2. A method as claimed in claim 1 in which the electrical output is translated into an audible output which is correlated with the internal feature with which the pig has made the impact.

3. A method as claimed in claim 1 in which the electrical output is translated into a visual output which is correlated with the internal feature with which the pig has made the impact.

4. A method as claimed in claim 2 in which the audible output is recorded.

5. A method as claimed in claim 3 in which the visual output is recorded.

6. A method as claimed in claim 2 in which the electrical output is filtered before translation to filter out frequencies lying outside the frequency band 8 Hz to 1560 Hz.

7. A method as claimed in claim 3 in which the electrical output is filtered before translation to filter out frequencies lying outside the frequency band 8 Hz to 1560 Hz.

8. A method as claimed in claim 1 in which the vibrational signals are detected and the electrical output produced by means of a geophone which is coupled to the external wall of the pipeline at the second point in the pipeline length.

* * * * *